United States Patent
Iguchi et al.

(10) Patent No.: US 7,948,627 B2
(45) Date of Patent: May 24, 2011

(54) PHOTOELECTRIC SMOKE DETECTOR

(75) Inventors: Masao Iguchi, Tokyo (JP); Kanji Numao, Tokyo (JP)

(73) Assignee: Fenwal Controls of Japan, Ltd., Tokyo (JP)

(*) Notice: Subject to any disclaimer, the term of this patent is extended or adjusted under 35 U.S.C. 154(b) by 0 days.

(21) Appl. No.: 12/748,192

(22) Filed: Mar. 26, 2010

(65) Prior Publication Data

US 2010/0176957 A1  Jul. 15, 2010

Related U.S. Application Data

(62) Division of application No. 11/910,210, filed as application No. PCT/JP2005/023022 on Dec. 15, 2005, now Pat. No. 7,697,140.

(30) Foreign Application Priority Data

Mar. 31, 2005  (JP) .................................. 2005-100590

(51) Int. Cl.
*G01N 21/00* (2006.01)
(52) U.S. Cl. ......... 356/438; 250/574; 340/628; 340/630
(58) Field of Classification Search .......... 356/432–440; 250/573, 574; 340/630, 628, 698.6, 693.12
See application file for complete search history.

(56) References Cited

U.S. PATENT DOCUMENTS

| | | | |
|---|---|---|---|
| 3,460,124 A * | 8/1969 | House et al. | 340/630 |
| 4,121,110 A * | 10/1978 | Solomon | 340/630 |
| 6,437,698 B1 * | 8/2002 | Byrne et al. | 340/630 |

FOREIGN PATENT DOCUMENTS

| | | |
|---|---|---|
| JP | 04-160698 | 6/1992 |
| JP | 07-057163 | 3/1995 |
| JP | 08-166347 | 6/1996 |
| JP | 08-293084 | 11/1996 |
| JP | 10-027288 | 1/1998 |
| JP | 10-027289 | 1/1998 |
| JP | 10-049769 | 2/1998 |

OTHER PUBLICATIONS

PCT International Search Report, Application No. PCT/JP2005/023022 by Fenwal Controls of Japan, Ltd., Search Report dated May 2, 2006.

* cited by examiner

*Primary Examiner* — Hoa Q Pham
(74) *Attorney, Agent, or Firm* — SoCal IP Law Group LLP; Steven C. Sereboff; John E. Gunther

(57) ABSTRACT

A photoelectric smoke detector may detect presence of smoke by utilizing a light emitting element and a light receiving element whose optical axes intersect with each other. The photoelectric smoke detector may include a casing for storing the light emitting element and the light receiving element. Inlet and outlet ports may be respectively provided in one and the other sides of the casing, the inlet and outlet ports bringing air flow into the casing. Rectifying light blocking means may be provided contiguously with each of the inlet and outlet ports, the rectifying light blocking means preventing entry of disturbance light into an interior space and forming a flow line of smoke extending from one or the other inlet and outlet port to the other or the one inlet and outlet port such that the flow line passes through a detection area by the light emitting element and the light receiving element.

7 Claims, 7 Drawing Sheets

10 PHOTOELECTRIC SMOKE DETECTOR

10 PHOTOELECTRIC SMOKE DETECTOR

20 MOUNTAIN-LIKE LABYRINTH
21
22

(A)
1
2 CHAMBER PART
SMOKE (B)
5 LABYRINTH
4 LIGHT RECEIVING ELEMENT
DETECTION AREA AR
2
3 LIGHT EMITTING ELEMENT

PHOTOELECTRIC SMOKE DETECTOR

CROSS-REFERENCE TO RELATED APPLICATION

This application is a division of application Ser. No. 11/910,210, filed Sep. 28, 2007, which is a National Stage Application filed under 35 U.S.C. 371 claiming the benefit of priority to Patent Cooperation Treaty Application No. PCT/JP2005/023022, filed Dec. 15, 2005, which claims priority to Japanese Patent Application No. 2005-100590 filed Mar. 31, 2005, all of which full contents are incorporated herein by reference.

BACKGROUND OF THE INVENTION

1. Technical Field of the Invention

The present invention relates to a photoelectric smoke detector utilizing a light emitting element and a light receiving element.

2. Background Arts

Photoelectric smoke detectors used to mainly detect smoke associated with fire occurring in indoor space, but in recent years have come to be also used as one means adapted to quickly detect device abnormalities while being installed in a device, such as a semiconductor producing device, a machine tool, a switchboard, an industrial controller, or the like.

As described above, although installed in different targets, smoke detectors for use in a device also have the same configuration as that of the smoke detectors for use in indoor space, and many of them have been downsized while keeping this configuration.

FIG. 4 show a configuration of a conventional typical photoelectric smoke detector (see Patent Document 1 for example).

The conventional photoelectric smoke detector 1 is, for example, as shown in FIG. 4(A), installed on the ceiling or the like in such a manner that a chamber part 2 having a plurality of inlet and outlet ports circumferentially provided as smoke introduction and extraction ports are oriented downward so that the smoke travel direction can be disregarded. Inside the chamber part 2, as shown in FIG. 4(B), a light emitting element 3 and a light receiving element 4 are arranged so that optical axes intersect with each other at approximately 120 degrees. Smoke enters into a detection area AR located near the intersection between the optical axes, and light emitted from the light emitting element 3 is scattered by the smoke and reaches the light receiving element 4, thereby achieving detection of the presence of smoke. To prevent erroneous detection under an absence of smoke, a plurality of labyrinths 5 are arranged circumferentially so as to eliminate disturbance light, also even when light emitted from the light emitting element 3 is reflected, prevent this light from traveling toward the light receiving element 4, and further avoid preventing the entry of smoke into the detection area. Around the plurality of labyrinths 5, an insect screen 6 is provided for preventing entry of insects from entering into the interior space.

Moreover, there conventionally exists a photoelectric smoke detector, as described in Patent Document 2, which introduces smoke to an optical chamber through only one opening provided at a bottom surface and which detects the presence of smoke through functions of a light emitting element and a light receiving element provided on the left and right side surfaces of the optical chamber.

[Patent Document 1] Japanese Patent Laid-Open No. 1996-166347

[Patent Document 2] Japanese Patent Laid-Open No. 1992-160698

DISCLOSURE OF THE INVENTION

Problem to be Solved by the Invention

The configuration of the conventional smoke detector shown in FIG. 4, due to characteristics of a detection system in which the light emitting element 3, the light receiving element 4, and the labyrinth 5 are arranged circumferentially, requires some space including the detection area AR. In other words, it is difficult to achieve downsizing only by simply reducing a diameter of the chamber part 2 while maintaining the conventional configuration.

The smoke detector is large in size, which restricts its installation places, thus making it not easy to install the smoke detector at places, such as a place where fire is likely to occur, a place where smoke is likely to pass in the event of fire, and the like.

A conventional smoke detector as described in Patent Document 2 has an optical chamber with one opening, which makes it difficult for smoke to flow, thus possibly retarding detection on this surface.

In view of the points described above, the present invention has been made, and it is an object of the present invention to provide a photoelectric smoke detector suitable for being downsized without detection capability deterioration.

Means for Solving the Problems

To solve the problem described above, a first aspect of the invention refers to a photoelectric smoke detector for detecting the presence of smoke by utilizing a light emitting element and a light receiving element whose optical axes intersect with each other. The photoelectric smoke detector includes: (1) a specialized labyrinth function fulfilling part for playing only a labyrinth function of bringing air flow into an interior space thereof and preventing entry of disturbance light into the interior space; and (2) a smoke detecting part which is provided above the specialized labyrinth function fulfilling part so that an interior space of the smoke detecting part is communicated with the interior space of the specialized labyrinth function fulfilling part, and which has the light emitting element and the light receiving element built therein and has a small hole for extracting air flow that has passed through a detection area near an intersection between the optical axes of the light emitting element and the light receiving element.

A second aspect of the present invention refers to a photoelectric smoke detector for detecting presence of smoke by utilising a light emitting element and a light receiving element whose optical axes intersect with each other. The photoelectric smoke detector includes: a casing for storing the light emitting element and the light receiving element; inlet and outlet ports which are respectively provided in one and the other sides of the casing, and which brings air flow into the casing; and rectifying light blocking means which is provided contiguously with each of the inlet and outlet ports, and which prevents entry of disturbance light into an interior space and forms a flow line of smoke extending from one or the other inlet and outlet port to the other or the one inlet and outlet port while being made penetrate through a detection area by the light emitting element and the light receiving element.

Consequently, smoke that has flown in through any one of the inlet and outlet ports flows into the casing via the rectifying light blocking means. At this point in time, the rectifying light blocking means prevents entry of disturbance light into the interior space and also guides the smoke to the detection area described above.

EFFECTS OF THE INVENTION

According to the present invention, a specialized labyrinth function fulfilling part for playing only a labyrinth function and a smoke detector for playing a smoke detection function are separated from each other and arranged in the vertical. Thus, this permits achieving a photoelectric smoke detector suitable for being downsized without detection capability deterioration.

Moreover, the light emitting element and the light receiving element are stored in the casing and the inlet and outlet ports are provided, and also the rectifying light blocking means is respectively provided at the inlet and outlet ports, so that smoke is guided to the detection area while preventing entry of disturbance light into the interior space. Thus, further downsizing can be achieved without detection capability deterioration.

DETAILED DESCRIPTION OF THE INVENTION

Description of the Reference Numerals

Figure 1:
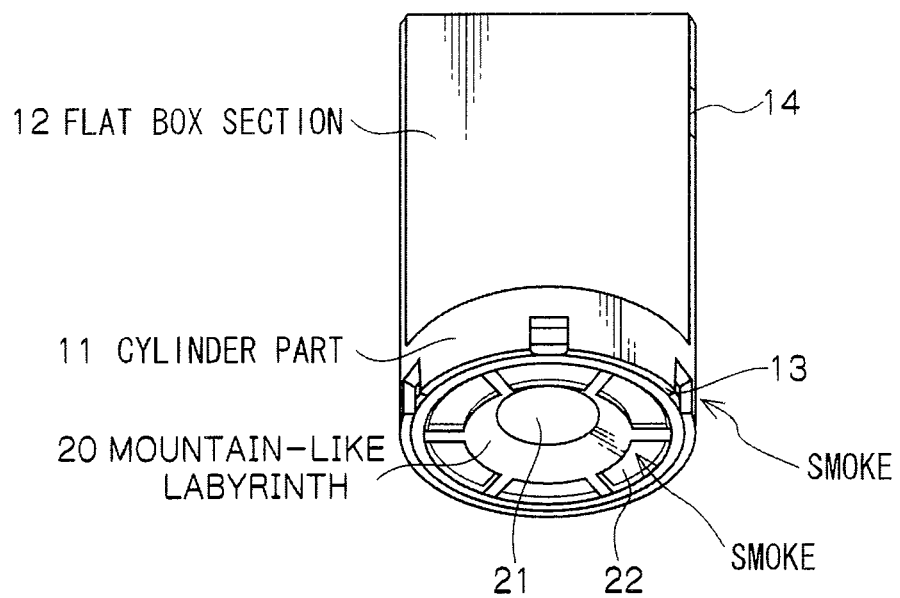
FIG. 1 is a perspective view showing a photoelectric smoke detector of a first embodiment of the present invention.

10 Photoelectric smoke detector
11 Circular cylinder part
12 Flat box part
14 Side small hole
20 Mountain-like labyrinth
30 Light emitting element
31a Upper inclined surface
40 Light receiving element
41a Lower inclined surface
41b Upper inclined surface
51 to 53 Labyrinth
100 Photoelectric smoke detector
101 Casing
102 One side end wall
105 Storage chamber
106 One side air chamber
107 The other side air chamber
108 Storage chamber side one side end wall
111, 112 Inlet and outlet port
115, 116 Rectification light blocking means
117 Inflow and outflow port
118 Insect screen

BEST MODE FOR CARRYING OUT THE INVENTION

Hereinafter, embodiments of the present invention will be described. A photoelectric smoke detector according to the present invention is applicable to a smoke detector installed in a place such as ordinary household, public facilities, or the like where people gather, a factory device such as a semiconductor producing device, a machining tool, a switchboard, an industrial controller, or the like, or any of other places where this photoelectric smoke detector has been hardly installed before.

(A) First Embodiment

Figure 2:
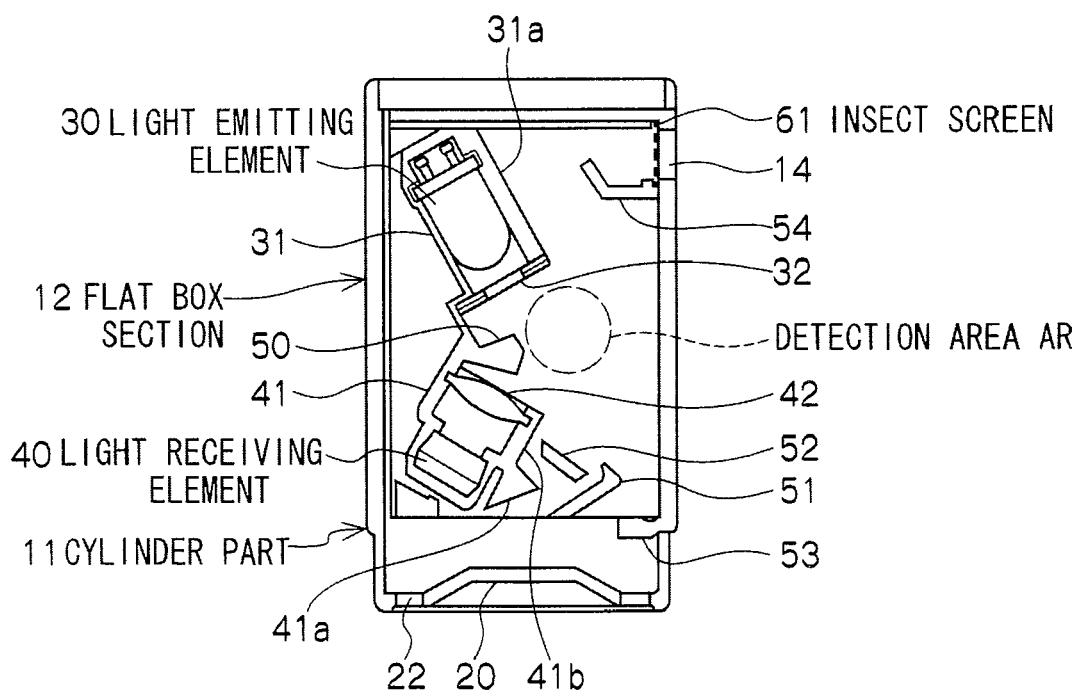
FIG. 2 is a longitudinal sectional view of the photoelectric smoke detector of the first embodiment of the present invention.

Hereinafter, one embodiment of the photoelectric smoke detector according to the present invention will be described in detail, referring to the drawings. FIG. 1 is a perspective view showing the photoelectric smoke detector of the embodiment. FIG. 2 is a longitudinal sectional view of the photoelectric smoke detector of the embodiment (a hatched line indicating the cross section is omitted).

The fitting directions of the smoke detectors of the embodiments are not limited to a direction shown in FIG. 1. However, in the following description, the top (upper), bottom (lower), left, and right are expressed, referring to a condition of FIG. 1.

The smoke detector 10 of the embodiment includes visually a circular cylinder part 11, and a flat box part 12 extending upwardly from the circular cylinder part 11.

The circular cylinder part 11 mainly plays a function of introducing smoke into the smoke detector 10 while preventing entry of disturbance light, insects, and the like into this smoke detector 10.

Figure 3:
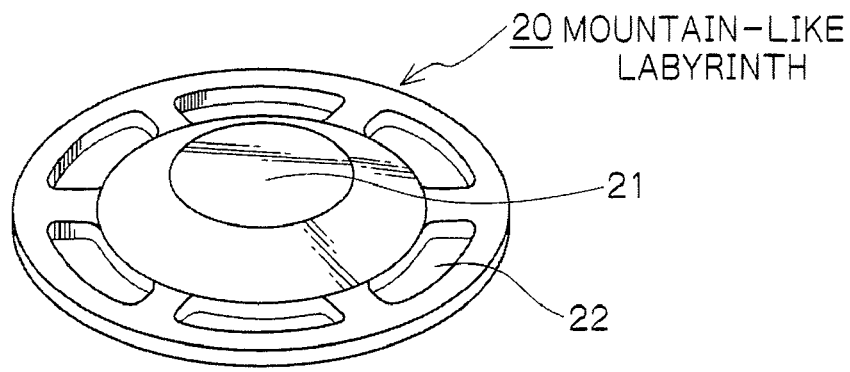
FIG. 3 is a perspective view showing a mountain-like labyrinth of the first embodiment of the present invention.

At the bottom opening of the circular cylinder part 11, a mountain-like labyrinth 20 is provided which has a mountain-like shape as shown in FIG. 3. The mountain-like labyrinth 20, as shown in FIG. 3, has a central part 21 ridged in a mountain-like shape and has, near a circumferential edge thereof, a plurality of (six illustrated in the figure) arc-shaped openings 22 provided circumferentially at equal intervals. The openings 22 of the mountain-like labyrinth 20 function as a smoke introduction port. The mountain-like central part 21 plays a function of upwardly guiding smoke introduced through the openings 22 of the mountain-like labyrinth 20 or side holes 13 of the circular cylinder part 11 to be described later and a function of preventing entry of disturbance light.

At the lower position of a side surface (outer circumferential surface) of the circular cylinder part 11, a plurality of (five illustrated in the figure) small holes 13 are provided circumferentially at equal intervals. The area of the small hole 13 permits smoke introduction from the side and is so selected as to minimize entry of disturbance light through this small hole 13.

The flat box part 12 is substantially rectangular-parallelepiped-shaped, and mainly plays a smoke detection function with its inner configuration. A width of the flat box part 12 is equal to an outer diameter of the circular cylinder part 11. The flat box part 12 extends upwardly from the circular cylinder part 11 in such a manner that its own central axis and the central axis of the circular cylinder part 11 agree with each other.

In a right side surface of the flat box part 12 near the top surface thereof, a side small hole 14 of the flat box part 12 is provided. This side small hole 14 functions as an opening upon smoke extraction from the inside to outside of the smoke detector 10. Specifically, smoke introduced into the smoke detector 10 through the openings 22 of the mountain-like labyrinth 20 or the side small holes 13 of the circular cylinder part 11 is extracted through the side small hole 14 of the flat box part 12. The above description refers to a flow of smoke intended by the inventor. However, in practice, smoke may flow in a reversed route.

Inside the smoke detector 10 (more precisely, inside the flat box part 12) of the embodiment, as shown in FIG. 2, a light emitting element 30 and a light receiving element 40 are provided.

The light emitting element 30 is provided at the upper left position in the interior space of the flat box part 12 by a light emitting element storage part 31. The light emitting element storage part 31 stores the light emitting element 30 with almost no gap therebetween in such a manner as to emanate light emitted from the light emitting element 30 only forward. In front of the light emitting element storage part 31, an optical window 32 is provided. The optical window 32 may be a simple opening playing a narrowing-down function. Further the optical window 32 may be such glass that achieves a dust-proofing function.

The light receiving element 40 is provided at the lower left position in the interior space of the flat box part 12 by a light receiving element storage part 41. The light receiving element storage part 41 has a circular-cylindrical interior space, and stores the light receiving element 40 at the bottom thereof and has an objective lens 42 fitted on the top thereof.

An optical axis of the light emitting element 30 and an optical axis of the light receiving element 40 intersect with each other at an angle of approximately 120 degrees, and the vicinity of this intersection serves as a detection area AR for smoke. Specifically, the presence of smoke in this detection area causes light emitted from the light emitting element 30 to be scattered by the smoke, and this scattering light reaches the light receiving element 40, which permits the detection of the presence of smoke.

On the immediate left position of the detection area AR, a direct light preventing labyrinth 50 is provided which prevents light emitted from the light emitting element 30 from reaching the light receiving element 40 without scattering.

At the boundary between the circular cylinder part 11 and the flat box part 12 in the interior space of the smoke detector 10, a lower insect screen 60 is provided. This lower insect screen 60 is circular-shaped when provided on a circular cylinder part 11 side and has a rectangular shape when provided on a flat box part 12 side. The lower insect screen 60 is provided for preventing insects entering through the openings 22 of the mountain-like labyrinth 20 or the side small holes 13 of the circular cylinder part 11 from entering further inside.

The distance between the mountain-like labyrinth 20 and the lower insect screen 60, in other words, the height of the circular cylinder part 11 is selected at a distance so that the function of upwardly guiding smoke by the mountain-like labyrinth 20 can be fully fulfilled.

Above near the lower insect screen 60 and also on the right of the light receiving element storage part 41, two labyrinth pieces 51 and 52 are provided which are arranged in the vertical. A pressing piece for the lower insect screen 60 located on the right also functions as a labyrinth piece 53. The labyrinth piece 51 is oriented diagonally right up, and rightwardly and upwardly guides air flow from the lower side by the bottom surface thereof. The upper end part of the labyrinth piece 51 is bent leftward and upward, fulfilling a function of directing air flow rising along the top surface thereof toward a detection area. The labyrinth piece 52 is provided at the upper left position of the labyrinth piece 51 in a manner such as to be oriented diagonally left up. The labyrinth piece 52 leftwardly and upwardly guides a direct air flow from the central part of the lower insect screen 60, air flow traveling along an inclination of a lower inclined surface 41*a* of the light receiving element storage part 41, and the like. In this direction, an upper inclined surface 41*b* of the light receiving element storage part 41 is provided. An air flow directed to the upper inclined surface 41*b* of the light receiving element storage part 41 is directed toward the detection area AR by this upper inclined surface 41*b*.

On the inner side of the side small hole 14 of the flat box section 12, an upper insect screen 61 is provided. The upper insect screen 61 prevents entry of insects through the side small hole 14.

A labyrinth piece 54 is provided which extends substantially leftward from the lower end position of the side small hole 14 of the flat box part 12. This labyrinth piece 54 is so bent as to be directed leftward and upward from the central position thereof. Air flow passing through the detection area AR and further rising is adapted to be narrowed down by an upper inclined surface 31*a* of the light emitting storage part 31 and the bottom inclined surface of the labyrinth piece 54, then reaches the top side of the interior space, is directed by subsequent air flow pressure toward the side small hole 14, and then is extracted through the side small hole 14.

The presence of the mountain-like labyrinth 20 greatly reduces entry of disturbance light from the lower side, the metallic lower insect screen 60 also reduces the entry of disturbance light form the lower side, and the lower inclined surface 41*a* of the light receiving element storage part 41 and the labyrinth pieces 51 to 53 further prevents this entry. Even if disturbance light passes through portions of the lower inclined surface 41*a* of the light receiving element storage part 41 and the labyrinth pieces 51 to 53, its travel direction is substantially upward, while the light receiving element 40 is provided inside the light receiving element storage part 41, plus at the bottom thereof, so that such disturbance light does not reach the light receiving element 40.

The side small hole 14 of the flat box part 12 has a small area and thus restricts entry of disturbance light therethrough, and the upper insect screen 60 that covers this side small hole 14 from the inside also restricts the entry of disturbance light. The labyrinth piece 54 has a sufficient length and also is inclined leftward and upward from the center thereof, and thus can direct entering disturbance light upward, thus eliminating those directed to the light receiving element 40 side almost completely. Even if the disturbance light travels further ahead of a tip end of the labyrinth piece 54 as a result of its reflection or the like, its travel direction is directed by the upper inclined surface 31*a* of the light emitting storage part 31 in the direction not toward the light receiving element 40.

With the photoelectric smoke detector of the embodiment described above, the number of labyrinths is small and the flat box part plays a main role in detection, which permits achieving downsizing. An electric processing construction can also be provided on one surface of the flat box part, which does not disturb the downsizing. The circular cylinder part 11 mainly fulfills a labyrinth function, which permits reducing the number of labyrinths provided in the flat box part 12.

That is, one characteristic of the present embodiment is that a portion (circular cylinder part 11) specialized for a labyrinth function is provided in which a light emitting element, a light receiving element, and a detection area do not exist.

Moreover, an introduction port and an extraction port for air flow are both provided, so that an air flow passes through the inside of the smoke detector, which permits achieving a higher detection accuracy than is achieved in a case where only an opening serving as both the introduction port and the extraction port is provided. Although a stream of air flow inside the flat box part is substantially constant, the presence of the circular cylinder part 11, and the presence of the mountain-like labyrinth 20 in particular, permits introducing to the inside the air flow around the smoke detector 10 directed in any direction, which in turn permits improving the detection accuracy.

Further, a simple configuration with a small number of labyrinths is provided, which not only permits easy manufacture but also holds the promise for low costs.

The smoke detector of the present embodiment is applicable as both a smoke detector for use in a device and a smoke detector for use in the interior space, thus not limiting its application.

(B) Second Embodiment

In the embodiment described above, the one illustrated has an extraction hole (side small hole 14) for an air flow (smoke) provided at the upper right side surface thereof. However, the extraction hole for air flow (smoke) may be also given at another surface (top surface, another side surface, front surface, or back surface) in the number not limited to one.

Figure 4:
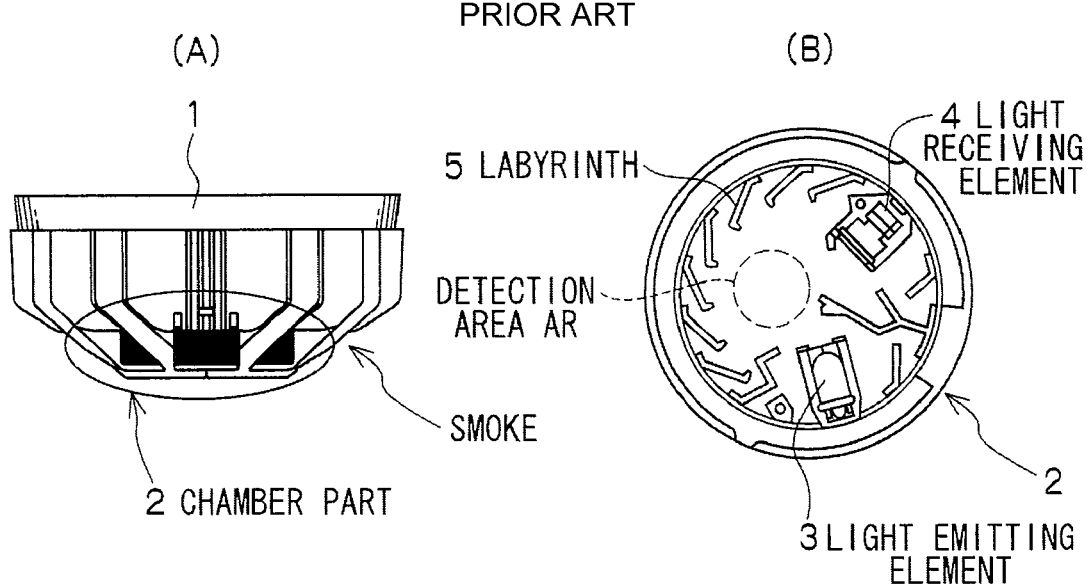
FIG. 4 are explanatory diagrams showing a conventional photoelectric smoke detector.

The aforementioned configuration of the circular cylinder part 11 illustrated serves as the portion specialized for the labyrinth function, although this configuration may be provided in different configuration. For example, from a configuration as shown in FIG. 4(B), a light emitting element and a light receiving element may be removed, and resulting a configuration with a smaller diameter may be applied as a portion specialized for a labyrinth function. Moreover, the portion specialized for a labyrinth function may also be formed in the shape of a flat box, which may be integrated with the flat box part 11 of the embodiment described above.

It is needless to say that the number of labyrinths in the flat box part 12 and the positional relationship between the light emitting element 30 and the light receiving element 40 are not limited to those of the embodiment described above. For example, the light emitting element 30 may be provided on a lower side and the light receiving element 40 may be provided on an upper side.

The photoelectric smoke detector of the present invention is intended to be used in a manner such that the portion specialized for fulfilling the labyrinth function is provided on the lower side thereof. The scope of claims expresses a vertical based on the premise of such installation, but it is needless to say that the photoelectric smoke detector may be so installed as to be oriented in another direction.

(C) Third Embodiment

Figure 5:
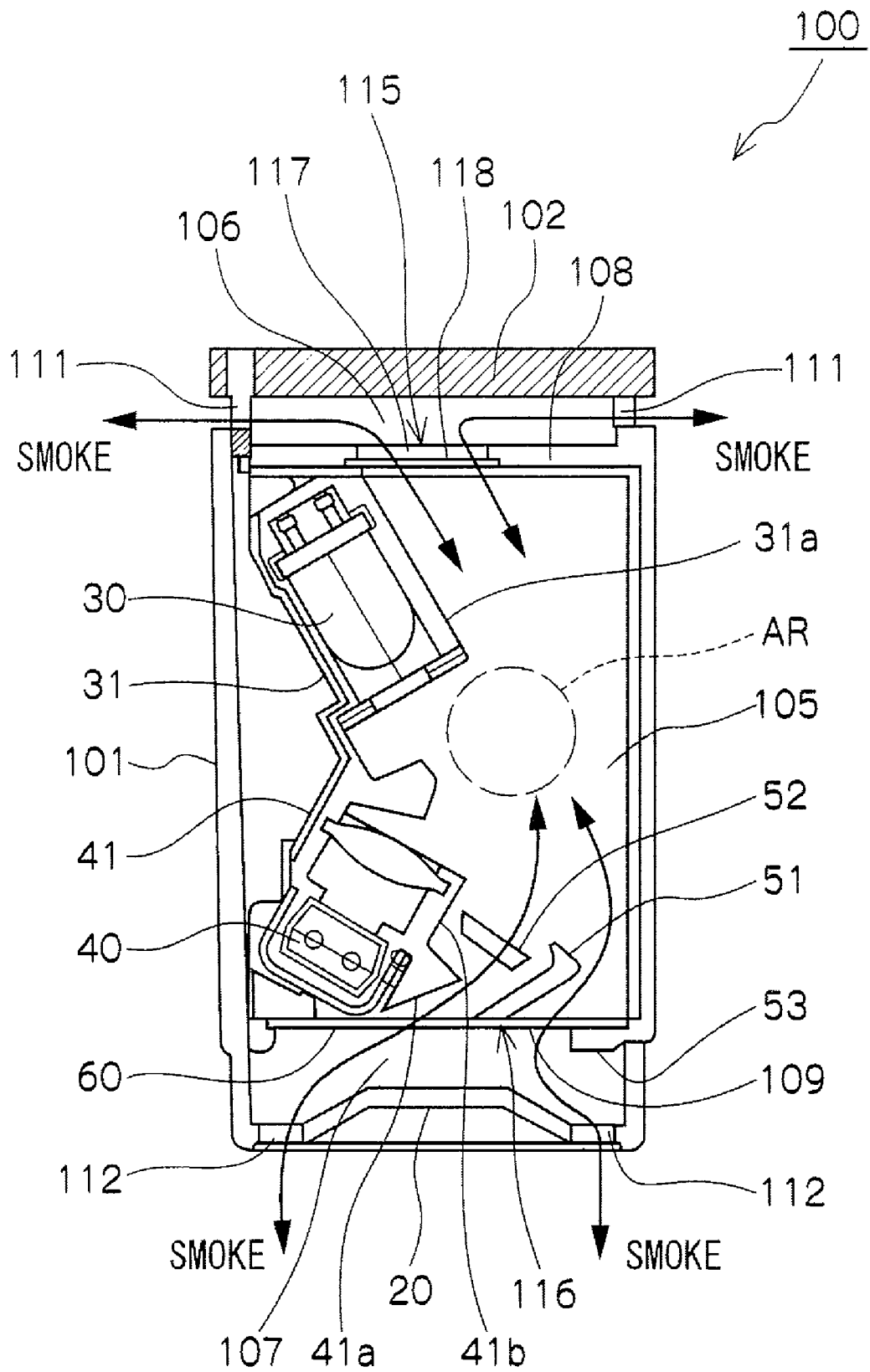
FIG. 5 is a longitudinal sectional view of a photoelectric smoke detector of a third embodiment of the present invention.
Figure 6:
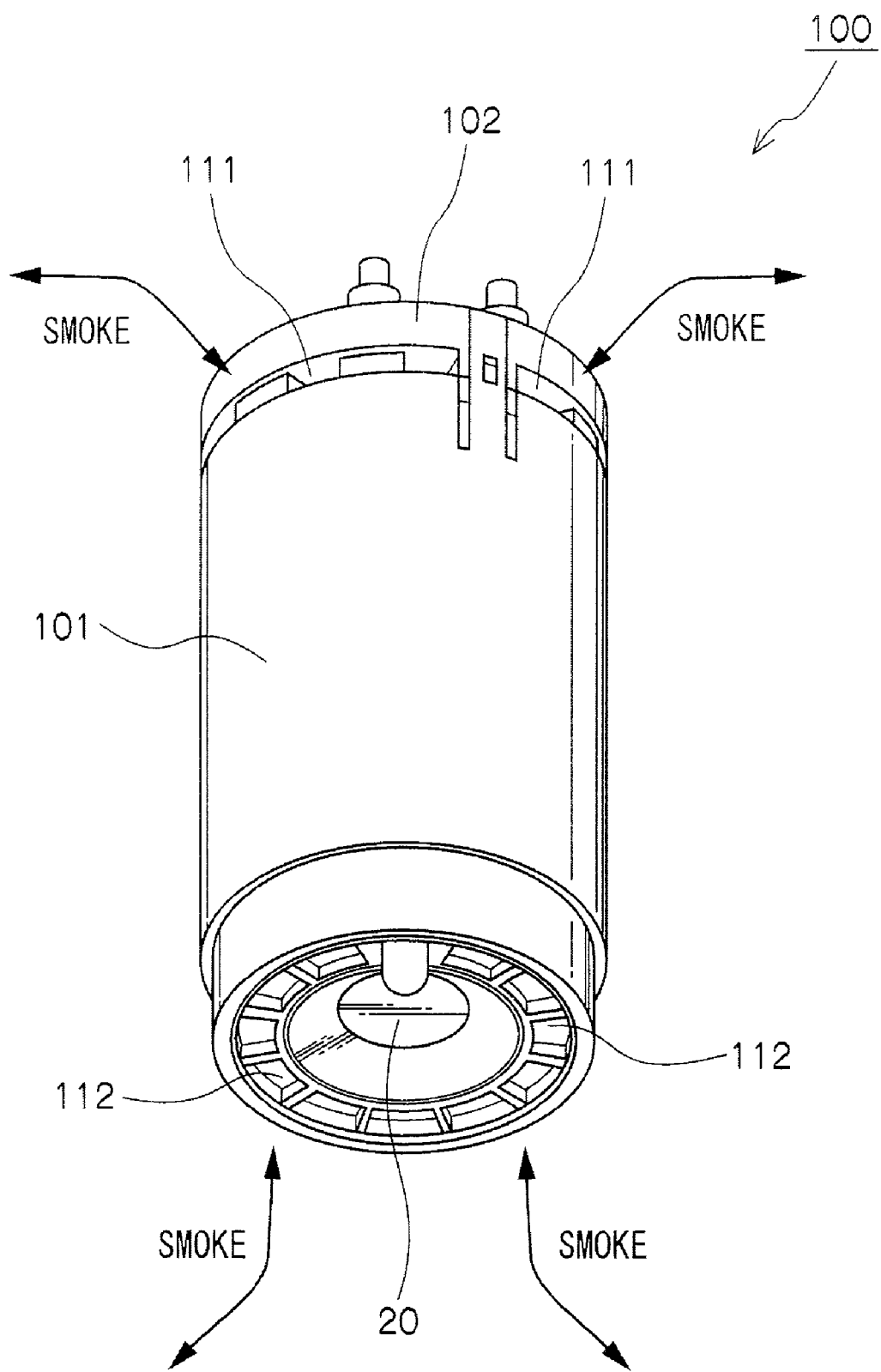
FIG. 6 is a perspective view of the photoelectric smoke detector of the third embodiment of the present invention.

Next, a third embodiment will be described referring to FIGS. 5 and 6. The present embodiment provides an even more downsized version of the photoelectric smoke detector 100 with an improved casing portion.

The photoelectric smoke detector 100 of the present embodiment is, as shown in the figures, mainly includes: the light emitting element 30, the light receiving element 40, and the like; and a casing 101. The light emitting element 30, the light receiving element 40, and the like are the same as those of the photoelectric smoke detector of the first embodiment.

The entire casing 101 is formed into a circular-cylindrical shape. This casing 101 is very small in size and set at a dimension that is slightly larger than a dimension including the light emitting element 30, the light emitting element storage part 31, the light receiving element 40, the light receiving element storage part 41, and a circuit board (not shown).

At one side end part of the casing 101 (the upper end part in FIG. 5), a one side end wall 102 is provided. This one side end wall 102 encloses a one side air chamber 106 to be described later and serves as a substrate supporting the entire photoelectric smoke detector 100. On the outer side surface of this one side end wall 102, an end wall fixing tool (not shown) for fixing the entire photoelectric smoke detector 100 is provided. This end wall fixing tool is a fixing tool for fixing the photoelectric smoke detector 100 to a ceiling plate, the wall, or the like inside the room. In addition, on the outer circumferential surface of the one side end wall 102 (outer circumferential surface of the circular-cylindrical casing 101), a circumferential edge fixing tool (not shown) for fixing the entire photoelectric smoke detector 100 is provided. This circumferential edge fixing tool is fixing means adapted to fix the photoelectric smoke detector 100 along the wall surface. Consequently, the photoelectric smoke detector 100 is fixed along or perpendicularly to the wall surface in accordance with a condition of an installation position. Further, the end wall fixing tool and the circumferential edge fixing tool may be so configured as to fix the photoelectric smoke detector 100 by adjusting it at an arbitrary angle, such as a longitudinal, lateral, or diagonal angle. As these end wall fixing tool and circumferential edge fixing tool, any of fixing tools with structure that can be typically used by those skilled in the art can be used.

The inside of the casing 101 includes a storage chamber 105, a one side air chamber 106, and other side air chamber 107.

The storage chamber 105 is a space for storing: the light emitting element 30, the light emitting storage part 31, the light receiving element 40, and the light receiving element storage part 41 including a detection area AR; a circuit board therefor; and the like. The storage chamber 105 is set at a dimension substantially equal to the entire dimension of the light emitting element 30 and the like. Further, this storage chamber 105 forms a smoke passage. Smoke flowing in the one side air chamber 106 or the other side air chamber 107 from the outside passes through the storage chamber 105 and then flows in the other side air chamber 107 or the one side air chamber 106. Then, at this point in time, in the storage chamber 105, a flow line of the smoke is so configured as to be made penetrate through the detection area AR by rectifying light blocking means 115 and 116 to be described later.

The light emitting element 30 and the light receiving element 40 are disposed along the central axis direction of the cylindrical casing 101 (longitudinally) in the storage chamber 105. Orienting them in this direction prevents the diameter of the cylindrical casing 101 from becoming large.

The one side air chamber 106 is a space for temporarily reserving external air taken in through an inlet and outlet port 111 to be described later and then delivering it to the one side rectifying light blocking means 115 to be described later. The one side air chamber 106 is provided between the inlet and outlet port 111 and the one side rectifying light blocking means 115. More specifically, the one side air chamber 106 is provided at a position adjacent to the one side (upper side in FIG. 5) of the storage chamber 105. The one side air chamber 106 is formed by being enclosed by a storage chamber side one side end wall 108 enclosing the one side end of the storage chamber 105 and the one side end wall 102 of the casing 101. These one side air chamber 106 and the storage chamber 105 are communicated with each other via the one side rectifying light blocking means 115 to be described later.

The other side air chamber 107 is a space for temporarily reserving external air taken in through an inlet and outlet port 112 to be described later and then delivering it to the other side rectifying light blocking means 116 to be described later. The other side air chamber 107 is located on the other side (lower side in FIG. 5) of the storage chamber 105, and provided between the inlet and outlet port 112 and the other side rectifying light blocking means 116. These the other side air chamber 107 and the storage chamber 105 are communicated with each other via the other side rectifying light blocking means 116 to be described later. The outer side surface (lower side surface) of the other side air chamber 107 serves as the mountain-like labyrinth 20. This mountain-like labyrinth 20 is identical to that of the first embodiment.

At one and the other end parts of the circular-cylindrical casing 101, the inlet and outlet ports 111 and 112 are respectively provided. These inlet and outlet ports 111 and 112 are openings for bringing external air flow into the casing 101. More specifically, the inlet and outlet ports 111 and 112 are so provided as to face the one side air chamber 106 and the other side air chamber 107, respectively. The one side inlet and outlet port 111 is formed by a plurality of holes provided over the entire circumference of the outer circumferential edge of the one side air chamber 106. Through this one side inlet and outlet port 111, external air flows into the one side air chamber 106 from the surrounding thereof. The other side inlet and outlet port 112 is formed by a plurality of holes provided over the entire circumference of the lower side surface part of the other side air chamber 107. Through this the other side inlet and outlet port 112, external air flows into the other side air chamber 107 from the lower side surface thereof. Consequently, the one side inlet and outlet port 111 and the other side inlet and outlet port 112 are so provided as to open in mutually orthogonal directions. This is intended to cause smoke flowing to the photoelectric smoke detector 100 from any direction to flow in either of the inlet and outlet ports 111 and 112.

Between the one side air chamber 106 and the storage chamber 105, the one side rectifying light blocking means 115 is provided. This one side rectifying light blocking means 115 is means adapted to prevent entry of disturbance light into the interior space (storage chamber 105) and also form, in cooperation with the other side rectifying light blocking means 116, a flow line of smoke which has penetrated through the detection area AR described above. This flow line of smoke is so formed as to flow through the one side inlet and outlet port 111 into the storage chamber 105 via the one side air chamber 106, penetrate through the detection area AR described above, and extend to the other side inlet and outlet port 112 via the other side air chamber 107. More specifically, the one side rectifying light blocking means 115 is formed by an inflow and outflow port 117 provided at the central part of the one side air chamber 106 and the upper inclined surface 31a of the light emitting storage part 31. This upper inclined surface 31a is adapted to rectify air (smoke) which has been once reserved in the one side air chamber 106 and then has flown into the storage chamber 105 after being narrowed down by the inflow and outflow port 117, and then guide it to the detection area AR. Further, locating the inflow and outflow port 117 at the central part of the one side air chamber 106 blocks light entering through the one side inlet and outlet port 111 by reflecting it into the one side air chamber 106 so that this light does not enter into the storage chamber 105. The inflow and outflow port 117 is provided with an insect screen 118.

The other side rectifying light blocking means 116, similarly to the one side rectifying light blocking means 115, is means adapted to prevent entry of disturbance light into the interior space (storage chamber 105) and also form, in cooperation with the one side rectifying light blocking means 115, a flow line of smoke which has penetrated through the detection area AR described above. The other side rectifying light blocking means 116 is provided at such a position as to face the one side rectifying light blocking means 115 with the detection area AR therebetween. Further, the other side rectifying light blocking means 116 is so configured as to rectify smoke flowing into the storage chamber 105 while blocking light so that this flow line penetrates through the detection area AR described above. This flow line of smoke, contrary to the case described above, is so formed as to flow through the other side inlet and outlet port 112 into the storage chamber 105 via the other side air chamber 107, penetrate through the detection area AR described above, and extend to the one side inlet and outlet port 111 via the one side air chamber 106. More specifically, the other side rectifying light blocking means 116 includes: labyrinths 51 to 53 provided at an inflow and outflow port 109; and the lower inclined surface 41a; and the upper inclined surface 41b. Further, the labyrinths 51 to 53 block light entering through the other side inlet and outlet port 112 to prevent entry of the light into the detection area AR. Between the storage chamber 105 and the other side air chamber 107, an insect screen 60 is provided.

The photoelectric smoke detector 100 configured as described above operates in the following manner.

First, the photoelectric smoke detector 100 is fitted to the ceiling plate, the room wall, or the like via the end wall fixing tool and circumferential edge fixing tool of the one side end wall 102. The photoelectric smoke detector 100 is small in size; thus, it is not site-specific in terms of fitting in particular and thus fitted at such a position that does not interfere with passage, operation, and the like. It is desirable that, in the event of fire, the photoelectric smoke detector 100 be fitted at a position serving as a smoke passage.

Next, upon flow of generated smoke to the photoelectric smoke detector 100, the smoke first enters into the photoelectric smoke detector 100 through the one side inlet and outlet port 111 or the other side inlet and outlet port 112.

The smoke entering through the one side inlet and outlet port 111 is reserved in the one side air chamber 106 and flows into the storage chamber 105 after being narrowed down at the inflow and outflow port 117. The smoke flowing into the storage chamber 105 is guided by the upper inclined surface 31a to pass through the detection area AR, flows to the other side air chamber 107 through the other side rectifying light blocking means 116, and flows out to the outside through the other side inlet and outlet port 112.

Then the smoke passing through the detection area AR is detected by the light emitting element 30 and the light receiving element 40, activating an alarm or the like.

The smoke entering through the other side inlet and outlet port 112 is reserved in the other side air chamber 107, and guided by the other side rectifying light blocking means 116 to pass through the detection area AR, flows to the one side air chamber 106 through the one side rectifying light blocking means 115, and flows out to the outside through the one side inlet and outlet port 111.

Then the smoke passing through the detection area AR is detected by the light emitting element 30 and the light receiving element 40, activating the alarm or the like.

This consequently provides the same effect as is provided by the first embodiment described above and also the following effect.

The flow line of smoke is so configured as to be made penetrate through the detection area AR by the one side rectifying light blocking means 115 and the other side rectifying light blocking means 116 which are so disposed as to face each other with the detection area AR therebetween. Thus, smoke flowing into the storage chamber 105 can be effectively led to the detection area AR, thereby improving the detection accuracy.

The one side rectifying light blocking means 115 and the other side rectifying light blocking means 116 described above are so disposed as to face each other with the detection area AR described above therebetween, which permits configuration such that the flow line of smoke reliably penetrates through the detection area AR. Further, the casing 101 is formed into a cylindrical shape so that air easily enters thereinto. Thus, this permits a configuration such that a flow line of smoke is reliably formed with this cylindrical casing 101 and the one side rectifying light blocking means 115 and the other side rectifying light blocking means 116 respectively provided at the both ends of the cylinder, and also such that the flow line of smoke reliably penetrates through the detection area AR.

The casing 101 described above is formed into a cylindrical shape and the light emitting element 30 and the light receiving element 40 described above are disposed along the central axis direction of the cylindrical casing 101, thus permitting downsizing of the casing 101. Further, it is configured such that all the components are stored in the cylindrical casing 101, thus permitting further downsizing of the photoelectric smoke detector 100. That is, by storing the light emitting element 30 in the circular-cylindrical casing 101 along the central axis direction of the casing 101 and also by providing the one side rectifying light blocking means 115 and the other side rectifying light blocking means 116 at such a position in the casing 101 as to face each other with the detection area AR therebetween, a flow line of smoke passes through the detection area AR described above in a manner penetrating therethrough, the inlet and outlet ports and a flow line for smoke are confirmed, and the labyrinths and the insect screens are reduced in size, thus permitting further downsizing of the photoelectric smoke detector 100.

As a result, the photoelectric smoke detector 100 can be provided at various places. In particular, the photoelectric smoke detector 100 can be easily fitted in a place where it used not to be fitted due to its bulkiness, for example, near a place that is likely to become a cause of fire. This permits early detection of fire.

The inlet and outlet ports 111 and 112 described above are formed large, and also the air chambers 106 and 107 for temporarily reserving air taken in through the inlet and outlet ports 111 and 112 and then delivering it to the rectifying light blocking means 115 and 116 are provided between these inlet and outlet ports 111 and 112 and the rectifying light blocking means 115 and 116. Thus, this permits external air containing smoke to easily flow into the air chambers 106 and 107 through the inlet and outlet ports 111 and 112, be temporarily reserved in the air chambers 106 and 107, and then be efficiently delivered to the rectifying light blocking means 115 and 116.

Moreover, the one side inlet and outlet port 111 and the other side inlet and outlet port 112 are so provided as to open in the mutually orthogonal directions. Thus, this permits smoke flowing to the photoelectric smoke detector 100 from any direction to flow into the inside through either of the inlet and outlet ports 111 and 112, thereby improving the detection accuracy.

INDUSTRIAL APPLICABILITY

Figure 7:
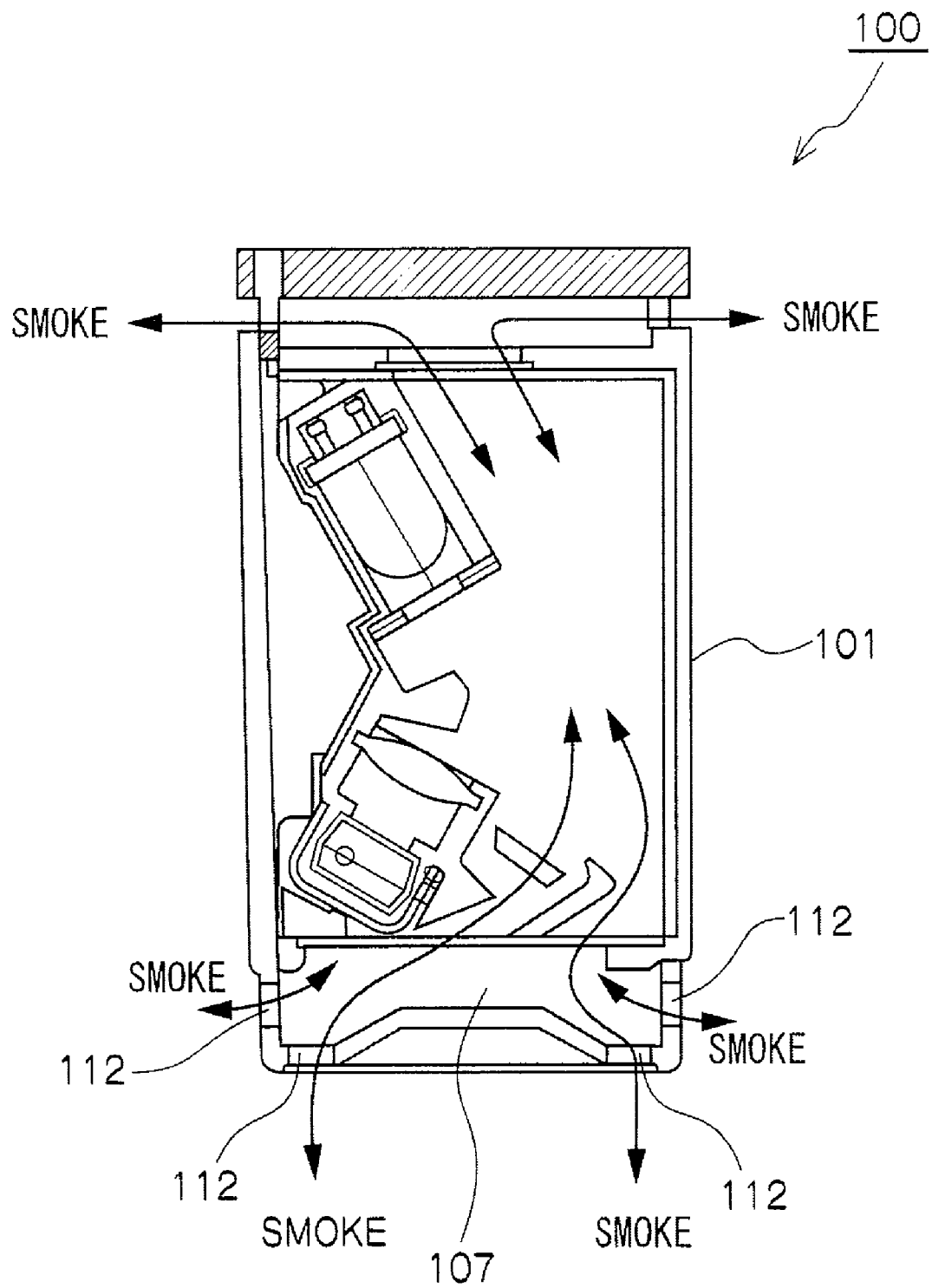
FIG. 7 is a longitudinal sectional view of a photoelectric smoke detector of a first modified example of the present invention.

In the embodiments described above, the other side inlet and outlet port 112 is provided at a lower side surface of the casing 101, but it may be, as shown in FIG. 7, provided, in addition to the lower side surface, on an outer circumferential edge part. This permits smoke flowing from any direction to flow into the other side air chamber 107. As a result, the smoke detection accuracy can be improved.

In the embodiments described above, the casing 101 is formed into a circular cylindrical shape, but it may be formed into any of cylindrical shapes, such as polygonal cylindrical shapes including a square cylindrical shape, a hexagonal cylindrical shape, and the like, and a barrel shape. Any of cylindrical shapes can be appropriately used which permits easy formation of a flow line penetrating through the detection area AR. In this case, the same operation and effects as are provided by the embodiments described above can be provided.

Figure 8:
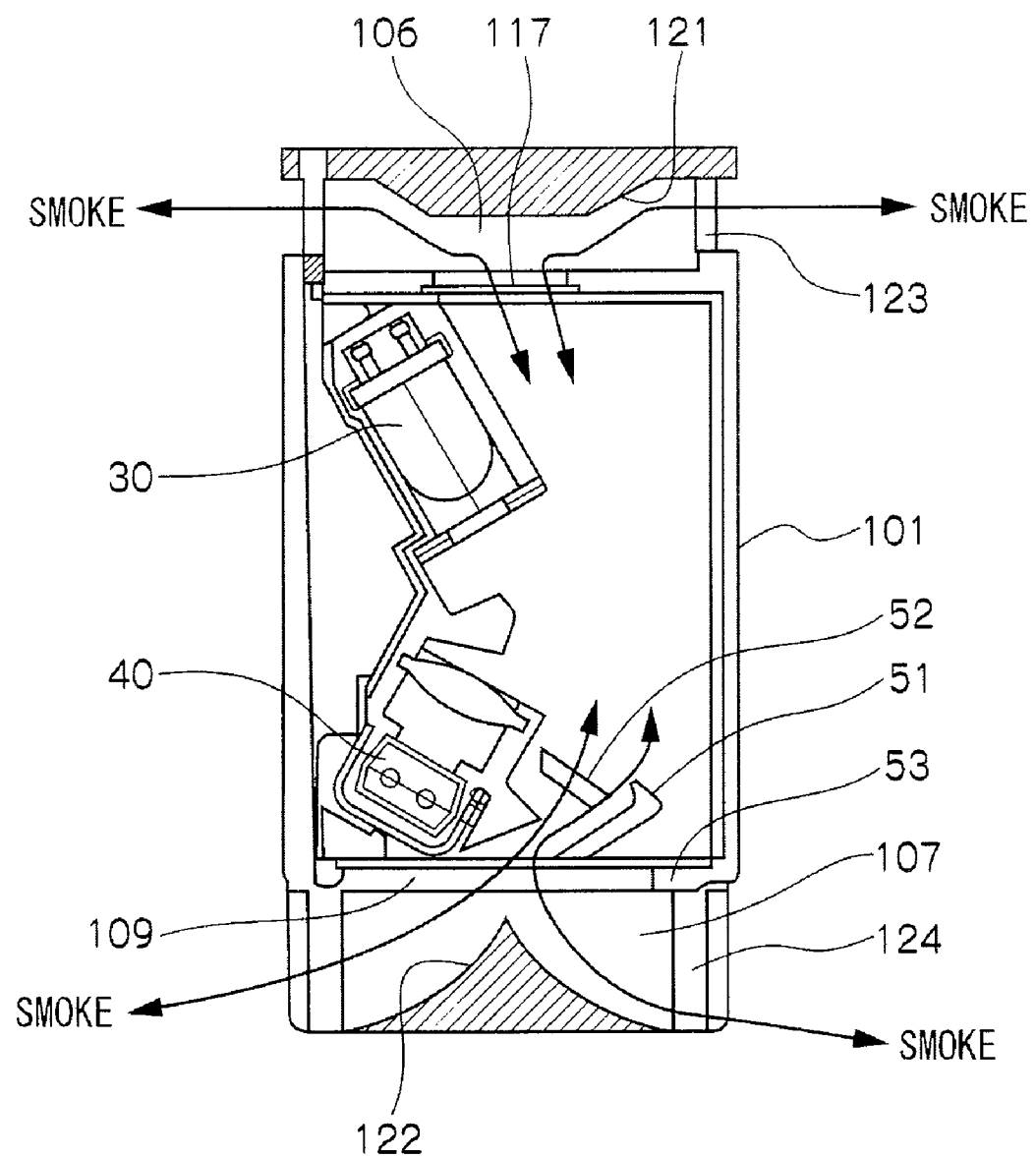
FIG. 8 is a longitudinal sectional view of a photoelectric smoke detector of a second modified example of the present invention.

In the embodiments described above, the one side air chamber 106 and the other side air chamber 107 are formed as spaces for temporarily reserving external air. However, as shown in FIG. 8, inflow guides 121 and 122 may be respectively provided in the one side air chamber 106 and the other side air chamber 107. The inflow guide 121 is formed into a truncated conical shape (trapezoidal shape cross-sectionally), and adapted to guide air flowing in through a surrounding inlet and outlet port 123 to the inflow and outflow port 117 by its conical surface. The inflow guide 122 is formed into a conical shape, and adapted to guide air flowing in through a surrounding inlet and outlet port 124 to the inflow and outflow port 109 by its conical surface.

Here, the inflow guide 121 is formed in the one side air chamber 106 so that the cross section of the inflow guide 121 is trapezoidal-shaped. However, the shape of this inflow guide 121 is set in accordance with various conditions, such as the dimension of the one side air chamber 106, the size of the inflow and outflow port 117, and the like. The inlet and outlet port 123 is formed larger than the inlet and outlet port 111 of the first embodiment, so that external light easily flows into the one side air chamber 106. Moreover, the light emitting element 30 and the like, and the labyrinths 51 to 53 are integrally provided, thus achieving downsizing, which in turn achieves downsizing of the entire photoelectric smoke detector 100.

The inflow guide 122 of the other side air chamber 107 is formed into a substantially conical shape with its cross section bent in a triangular shape. This bent portion is intended to make it easy for external air (smoke) flowing into the other side air chamber 107 to flow toward the inflow and outflow port 109. The shape of this inflow guide 122 is set in accordance with various conditions, such as the dimension of the other side air chamber 107, the size of the inflow and outflow port 119, and the like. The inlet and outlet port 124 is formed larger than an outer circumferential surface of the casing 101, thereby making it easy for external air to flow into the other side air chamber 107. As a result, the same operation and effect as are provided by the third embodiments described above can be provided.

Figure 9:
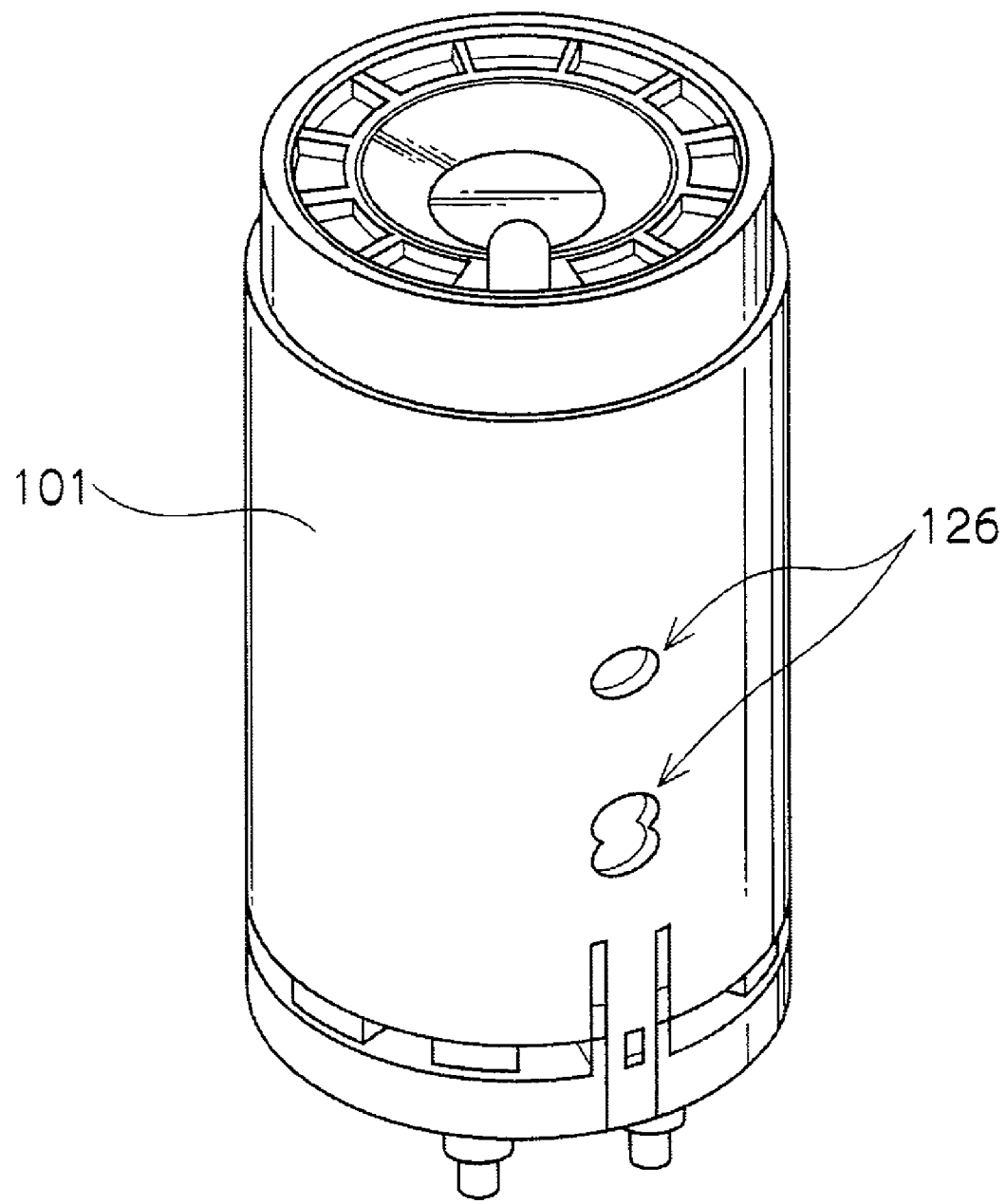
FIG. 9 is a perspective view of a photoelectric smoke detector of a third modified example of the present invention.

Moreover, in the embodiments described above, the storage chamber 105 is configured to be isolated from external air so that external light does not enter inside. However, as shown in FIG. 9, a sensitivity adjustment part 126 may be provided. This sensitivity adjustment part 126 is formed by a hole provided in the casing 101. The size, position, and the like of this hole are appropriately set to adjust the sensitivity of the light emitting element 30 and the light receiving element 40.

It is claimed:

1. A photoelectric smoke detector for detecting presence of smoke by utilizing a light emitting element and a light receiving element whose optical axes intersect with each other, the photoelectric smoke detector comprising:
   a casing for storing the light emitting element and the light receiving element;
   inlet and outlet ports respectively provided in one and another sides of the casing, the inlet and outlet ports bringing air flow into the casing;
   respective rectifying light blocking means provided contiguously with each of the inlet and outlet ports, the rectifying light blocking means preventing entry of disturbance light into an interior space and forming a flow line of smoke extending from one of the inlet and outlet ports to the other of the inlet and outlet ports, the flow line passing through a detection area by the light emitting element and the light receiving element; and
   respective air chambers disposed between the inlet and outlet ports and the respective rectifying light blocking means, the air chambers temporarily reserving air taken in through the inlet and outlet ports and then delivering the air to the rectifying light blocking means.

2. The photoelectric smoke detector according to claim 1, wherein the rectifying light blocking means are disposed to face each other with the detection area therebetween.

3. The photoelectric smoke detector according to claim 2, wherein the casing is formed into a cylindrical shape, and the light emitting element and
the light receiving element are disposed along a central axis direction of the cylindrical casing.

4. The photoelectric smoke detector according to claim 1, wherein the casing is formed into a cylindrical shape, and the light emitting element and the light receiving element are disposed along a central axis direction of the cylindrical casing.

5. The photoelectric smoke detector according to claim 1, wherein at least one of the rectifying light blocking means comprises:
   an inflow and outflow port disposed facing the detection area; and
   a labyrinth proximate the inflow and outflow port, the labyrinth preventing entry of disturbance light into the interior space and guiding external air flowing in through the inflow and outflow port to the detection area.

6. The photoelectric smoke detector according to claim 5, wherein each air chamber comprises an inflow guide for guiding air flowing in through the inlet and outlet port to the inflow and outflow port.

7. The photoelectric smoke detector according to claim 1, wherein the inlet port and the outlet port open in mutually orthogonal directions.

* * * * *